United States Patent [19]

Friesen et al.

[11] Patent Number: 5,015,730

[45] Date of Patent: May 14, 1991

[54] PREPARATION OF HOMOGENEOUS HUMAN FIBROBLAST INTERFERON

[75] Inventors: Heinz-Jürgen Friesen, Moers, Fed. Rep. of Germany; Sidney Pestka, North Caldwell, N.J.

[73] Assignee: Hoffmann-La Roche Inc., Nutley, N.J.

[21] Appl. No.: 386,088

[22] Filed: Jul. 14, 1989

Related U.S. Application Data

[60] Continuation of Ser. No. 691,989, Jan. 16, 1985, which is a continuation of Ser. No. 467,684, Feb. 18, 1983, abandoned, which is a continuation of Ser. No. 247,497, Mar. 25, 1981, now abandoned, which is a division of Ser. No. 160,889 filed Jun. 19, 1980 now U.S. Patent No. 4,289,689 issued Sep. 15, 1981, which is a continuation-in-part of Ser. No. 130,635 filed Mar. 14, 1980 now abandoned, which is a continuation-in-part of Ser. No. 62,371 filed Jul. 31, 1979 now abandoned.

[51] Int. Cl.$^5$ .................... C07K 15/26; A61K 31/66

[52] U.S. Cl. .................... 530/351; 424/85.6
[58] Field of Search .................. 530/351; 424/85.6

[56] References Cited

PUBLICATIONS

Knight Proc. Natl. Acad. Sci. 73:520–523 (1978).
Berthold et al., J. Biol. Chem. 253:5206–5212 (1978).
Reynolds et al., Biochem, Biophys, Res. Comm. 65(1) pp. 107–112 (1975).
Davey et al., J. of Biol, Chem. 251(23) pp. 7620–7625 (1976).

*Primary Examiner*—Margaret Moskowitz
*Assistant Examiner*—Shelly J. Guest
*Attorney, Agent, or Firm*—George M. Gould; William H. Epstein; Patricia S. Rocha

[57] ABSTRACT

Human fibroblast interferon has been purified to homogeneity by use of a novel procedure combining affinity chromatography and high pressure liquid chromatography (HPLC).

2 Claims, No Drawings

PREPARATION OF HOMOGENEOUS HUMAN FIBROBLAST INTERFERON

RELATED APPLICATIONS

This is a continuation, of application Serial No. 06/691,989 filed Jan. 16, 1985 which is a continuation of Ser. No. 467,684 filed Feb. 18, 1983 now abandoned, which is continuation of Ser. No. 247,497 filed Mar. 25, 1981 now abandoned, which is a division of Ser. No. 160,889 filed Jun. 19, 1980 now U.S. Patent No. 4,289,689 issued Sep. 15, 1981, which is a continuation-in-part of Ser. No. 130,635 filed Mar. 14, 1980 now abandoned, which is a continuation-in-part of Ser. No. 62,371 filed Jul. 31, 1979 now abandoned.

BACKGROUND OF THE INVENTION

Purification of proteins has long been a problem in peptide chemistry. Techniques which have been employed include precipitation, gel filtration, ion exchange chromatography, gel electrophoresis, affinity chromatography, and many others too numerous to mention.

Schemes to isolate naturally occurring, high molecular weight proteins which are present in biological samples in extremely low concentrations have involved multi-step procedures utilizing assays of the aforementioned techniques. In a great number of such cases tremendous quantities of crude starting material must be accumulated and processed at high cost and usually with expenditure of great effort due to large losses of product in the later steps of the purification procedure.

A good case in point is the history of the numerous attempts to isolate and characterize interferon. Since its first discovery by Isaacs and Lindenmann in 1957, interferon whether of the leucocyte or fibroblast form has resisted the attempts of researchers at institutions throughout the world spanning over two decades to be isolated as a homogeneous peptide in amounts sufficient to allow characterization and identification of its specific biological and chemical properties.

In U.S. Pat. No. 3,699,222, which is directed to Isaacs and Lindenmann's original research with interferon, the purification of the active material is limited to ammonium sulphate precipitation followed by dialysis. Such procedures are relatively non-specific and thus the product obtained thereby is still in an extremely crude state.

A multi-step procedure for purifying interferon is disclosed in U.S. Pat. No. 3,414,651 utilizing selective adsorption on an amorphous, alumino-silicate, elution with iodine or thiocyanate solution, further precipitation of unwanted protein with aqueous HCl and then aqueous NaOH, precipitation of interferon from the basic solution with water-miscible solvents such as methanol, ethanol or acetone and finally chromatography of the redissolved interferon on an anion exchange resin such as DEAE cellulose to produce an interferon whose specific activity is indicated to have been enhanced 6,000 fold by the entire process. Specific interferons exemplified were chick and monkey interferon.

U.S. Pat. No. 3,800,035 describes a method for inducing interferon production in human leukocytes in the absence of serum. The leukocytes are primed with interferon, the serum removed by centrifugation, the white cells suspended in nutrient medium and induced with a suitable inducing agent. A similar disclosure for inducing interferon in cell cultures is provided in U.S. Pat. No. 3,951,740 with the added feature of providing enough L-glutamine during the priming phase to keep the cells in an active metabolic state.

A further purification variation is taught in U.S. Pat. No. 3,975,344 where a crude human fibroblast interferon solution derived from the incubation medium of the cell culture was purified by zonal density gradient ultracentrifugation. This technique was indicated to give higher yields and purification than obtained with the conventional procedure of column chromatography on Sephadex G-100.

Recent scientific papers directed to the purification and attempted characterization of interferons can be summarized as follows:

Knight, E. (1976) "Interferon: Purification and Initial Characterization from Human Diploid Cells," *Proc. Natl. Acad. Sci. U.S.A.* 73, 520-523.

Torma, E. T., and Paucker, K. (1976) "Purification and Characterization of Human Leukocyte Interferon Components," *J. Biol. Chem.* 251, 4810-4816.

Bridgen, P. J., Anfinsen, C. B., Corley, L., Bose, S., Zoon, K. C., Ruegg, U. Th., and Buckler, C. E. (1977) "Human Lymphoblastoid Interferon, Large Scale Production and Partial Purification," *J. Biol. Chem.* 252, 6585-6587.

DeMaeyer, J., Tovey, M. G., Gresser, I., and DeMaeyer, E. (1978) "Purification of Mouse Interferon by Sequential Affinity Chromatography on poly(U) and Antibody-agorose columns," *Nature* 271, 622-625.

Kawakita, M., Cabrer, B., Taira, H., Rebello, M., Slattery, E., Weideli, H., and Lengyel, P. (1978) "Purification of Interferon from Mouse Ehrlich Ascites tumor cells," *J. Biol. Chem.* 253, 598-602.

Berthold, W., Tan, C., and Tan, Y. H. (1978) "Purification and in vitro labeling of interferon from a human fibroblastoid cell line," *J. Biol. Chem.* 253, 5206-5212.

Jankowski, W. J., Davey, M. W., O'Malley, J. A., Sulkowski, E., and Carter, W. A. (1975) "Molecular Structure of Human Fibroblast and Leukocyte Interferons: Probe by Lectin- and Hydrophobic Chromatography," *J. Virology* 16, 1124-1130.

Davey, M. W., Sulkowski, E., and Carter, W. A. (1976) "Hydrophobic Interaction of Human, Mouse, and Rabbit Interferons with Immobilized Hydrocarbons," *J. Biol. Chem.* 251, 7620-7625.

Chadha, K. C., Sclair, M., Sulkowski, E., and Carter, W. A. (1978) "Molecular Size Heterogeneity of Human Leukocyte Interferon," *Biochemistry* 17, 196-200.

While several of the above papers contain claims to have purified mouse or human interferons to homogeneity none of the classical proofs of homogeneity of protein materials were given nor were any properties of the allegedly pure compounds described.

The use of high performance liquid chromatography for purification of proteins is generally known in the art. These references specifically describe ion exchange and size exclusion type columns in protein purification. See for example Regnier and Noel, J. Chromatog. Sci. 14, 316 (1976) and Chang et al., Anal. Biochem. 48, 1839 (1976).

The use of LiChrosorb RP-18 (octadecyl bound silica microparticle column) in reverse phase partition chromatography was successfully employed to purify peptides such as β-endorphin. Rubinstein et al. Proc. Natl. Acad. Sci., U.S.A. 74, 4969 (1977).

In U.S. Pat. No. 4,172,071 purification of various interferon solutions is accomplished by affinity chromatography over a Blue Dextran Sepharose column. No additional purification steps are disclosed and the interferon produced is indicated to contain a high content of products with interferon type activity freed to a major extent from contaminating proteins.

The purification of interferons, particularly human leukocyte interferon to homogeneity using high pressure liquid chromatography in the last stages is described in U.S. Pat. No. 4,503,035.

The partial characterization of three species of mouse interferons (MW=33,000; 26,000 and 20,000) is described by Cabrer et al., J. Biol. Chem. 254 (10); 3681 (1979).

DESCRIPTION OF THE INVENTION

The present invention relates to an improved process for purifying human fibroblast interferon and to the novel homogeneous human fibroblast interferon produced thereby.

The improved process of the present invention involves a combination of affinity chromatography and high pressure liquid chromatography steps to achieve efficient purification of human fibroblast interferon.

It has been known in the art to employ affinity chromatography as a procedural step in the purification of human fibroblast interferon. Thus Davey et al., J. Biol. Chem. 251, 7620 (1976) describe the use of Concanavalin A-Sepharose 4B affinity chromatography to produce purified human fibroblast interferon. Jankowski et al., Biochemistry 15, 5182 (1976) utilize Blue Dextran-Sepharose for the same purpose. However, the prior art did not utilize or suggest the use of high pressure liquid chromatography in conjunction with such affinity chromatography steps.

Use of affinity chromatography on crude human fibroblast interferon preparations results in about a 300–3,000 fold purification in a single step. Thus, the human fibroblast interferon produced by the affinity chromatography procedure has a specific activity of about $3 \times 10^6 - 10^7$ units/mg.

The use of Blue Dextran-Sepharose is the preferred method of carrying out the affinity chromatography step. This preference is based on the fact that such procedure provided substantially higher yields than the Concanavalin A-Sepharose 4B procedure and also provides a more stable product.

For the Concanavalin A-Sepharose 4B procedure the following protocol can be employed:

(a) 20–30 column volumes of crude human fibroblast interferon (specific activity ~ $10^4$ units/mg) in 5% fetal calf serum containing minimal essential medium [Eagle's (MEM) (Gibco #109)] are pumped onto a Concanavalin A column at a linear flow rate of from 30–60 cm/hr;

(b) wash with phosphate buffered saline (PBS)-buffer pH 7.2

(c) wash with PBS-0.1M α-methyl mannoside (α-MM); and (d) elute with PBS-0.1M α-MM containing 50% ethylene glycol.

The resulting purified interferon obtained from step (d) exhibits a specific activity of about $10^7$ units/mg with a recovery of about 10–30%.

A suitable protocol for utilizing Blue Dextran-Sepharose in the affinity chromatography step is as follows:

(a) 10–40 column volumes of culture supernatant (10–30,000 units/ml, 0.2–1 mg protein/ml) are adjusted to 1.25M NaCl by addition of saturated NaCl solution and then pumped on the column at a linear flow rate of 20–40 cm/hr;

(b) the column is washed with 5–15 column volumes of 1M NaCl/0.02–0.05M phosphate and then with 5–15 column volumes 1M NaCl/0.02–0.05M phosphate containing 15% glycol (pH 7.2); and (c) interferon is eluted with the 1M NaCl/0.02M phosphate 50% ethylene glycol (pH 7.2).

The resulting interferon has a specific activity of approximately $3 \times 10^6$ units/mg and can be obtained from this step in a recovery of about 80%.

The Blue Dextran-Sepharose employed in the above affinity chromatography step can be conveniently prepared by coupling Blue Dextran, i.e., Cibacron Blue F3GA coupled to Dextran, to cyanogen bromide-activated Sepharose 4B at pH 9.5.

The aforesaid coupling procedure, as well as the washing and ageing of the resin, the design of column loading and elution is important for obtaining maximum yield and highest degree of purity of the product human fibroblast interferon.

In cases where the interferon sample is harvested from a serum free medium purification to homogeneity is accomplished by one or two passages through a Blue-Sepharose-4B column eluting with a 30–50% (v/v) ethylene glycol buffered aqueous solution (pH 7.2).

In order to achieve further purification of the interferon produced in the affinity chromatography step the interferon is processed through one or more high pressure liquid chromatography steps with high resolution and high yield on a preparative scale. The liquid chromatography procedure utilizes columns containing a porous silica matrix to which cyclohexyl, octyl, octadecyl, phenyl, diphenyl or cyanopropyl groups are bonded. These columns, which can be used sequentially and under varying conditions of pH and organic solvent gradient, can purify human fibroblast interferon to homogeneity as determined by obtaining a single band on sodium dodecylsulfate (NaDodSO$_4$) polyacrylmide gel electrophoresis, a constant specific activity, and a single peak on HPLC with activity and protein levels superimposable and a single NH$_2$-terminal amino acid sequence.

The irregularly shaped, totally porous silica microparticle columns (particle size about 10 microns and a pore size of about 100 Å) having cyclohexyl, octyl, octadecyl, phenyl or cyanopropyl groups bound thereto used in the practice of the invention are articles of commerce. Suitable columns include the LiChrosorb columns marketed by EM Laboratories of Elmsford, N. Y. such as LiChrosorb RP-8 (octyl bonded) and Chromegabond columns marketed by E. S. Industries of Marlton, N. J. such as Chromegabond cyclohexyl or C-8 (octyl) columns. A suitable cyanopropyl bonded column is marketed by Laboratory Data Control, of Riviera Beach, Fla. under the trademark Spherisorb CN (5μ-80 Å). Details regarding the preparation of a diphenyl column are provided below in Example 7. Conditions employed with the 4.6×300 mm size columns were found to be applicable to the larger 9.6×500 mm size columns.

A convenient high pressure liquid chromatography system for utilizing the aforesaid columns is described in U.S. Pat. No. 4,116,046, inventor Stanley Stein.

In performing the instant process, the solution of the affinity chromatography purified human fibroblast interferon in aqueous buffer of pH 4–8 is passed through the silica matrix column. A preferred buffer for purposes of the present invention is 8% pyridine-8% formic acid, (v/v). Usually the procedure is carried out under pressure, preferably in the range of from about 50 to about 5,000 psi. The interferon is absorbed to the column and is then subsequently eluted in selective fashion using a gradient of an aqueous buffer plus varying amounts of a water miscible solvent. Suitable water miscible solvents for this purpose include alkanols such as n-propanol, iso-propanol, n-butanol, tert.-butanol, ethanol, methanol and the like. Particularly preferred for the elution of human fibroblast interferon is a mixture of propanol and butanol.

Fractionation of the eluate is accomplished by utilizing fraction collectors in a manner known per se with concomitant monitoring of the protein content in each fraction by peptide monitors operating at high sensitivity. A suitable system for this purpose is disclosed by Bohlen et al., Anal. Biochem. 67, 438 (1975). Note also U.S. Pat. No. 3,876,881.

The selection of the specific resin types to be employed in the high pressure liquid chromatography steps depends on the source and purity of the human fibroblast interferon starting material for this step. Thus material produced by affinity chromatography on a Concanavalin A-Sepharose column is conveniently purified to homogeneity by utilizing high pressure liquid chromatography on a cyclohexyl bonded silica column followed by an octyl bonded silica column. On the other hand when a Blue Dextran column is utilized in the affinity chromatography step, purification to homogeneity can be accomplished by one or more passages through an octyl bonded silica column or alternatively by passage through the octyl bonded silica column followed by passage through a cyanopropyl bonded silica column and then, if required, through a diphenyl bonded silica column. When a Blue Sepharose-4B column and a serum free preparation is employed, a single passage through an octyl bonded silica column will achieve a homogeneous preparation.

Due to the sensitivity of human fibroblast interferon activity in the presence of organic solvents, e.g. the propanols, butanol or 2-methoxyethanol at neutral pH, chromatography was performed at acidic pH. Since human fibroblast interferon has a more hydrophobic nature than leucocyte interferon and since there are other more hydrophobic proteins present in the partially purified fibroblast interferon preparations, a mixture of propanol and butanol was found to provide the preferred solvent for elution of reverse phase columns rather than n-propanol. Use of such mixture serves to limit the organic solvent concentration necessary for complete elution of all absorbed proteins and thus reduces artifacts occurring at high loading due to lower solubility of proteins.

The homogeneous human-fibroblast interferon obtained in accordance with the present invention was derived as a single peak in the last stage high performance liquid chromatography column and provided a single narrow band on sodium dodecyl sulfate (NaDodSO$_4$) polyacrylamide gel electrophoresis in the presence of 2-mercaptoethanol. Extraction of the gel gave a single peak of antiviral activity coinciding with the protein band. While any conventional antiviral assay for human fibroblast activity can be used for this purpose, a preferred assay procedure is described in U.S. Pat. No. 4,241,174.

The molecular weight of the homogeneous human fibroblast interferon as determined by the polyacrylamide gel procedure was approximately 20,500. The specific activity of this purified material was approximately $4 \times 10^8$ units/mg. Amino acid analysis of human fibroblast interferon showed a general similarity to that exhibited by homogeneous human leukocyte interferon (U.S. Pat. No. 4,503,035 but significant differences in the respective levels of proline, alanine, leucine and tyrosine were observed. Additionally, the partial sequence of the NH$_2$ terminus obtained on a sample of such homogeneous human fibroblast interferon was Met-Ser-Tyr-Asn-Leu-Leu-Gly-Phe-Leu-Gln-Arg-Ser-Ser Asn-Phe-Gln- . . . -Gln-Lys which is consistent with the sequence for positions 1-13 reported by Knight and Hunkapillar at the New York Academy of Sciences Conference on Regulatory Functions of Interferons, Oct. 23-26, 1979 and extends the known sequence through position 19.

Interferons have exhibited antiviral, antitumor, growth inhibition and immunosupression activity. These activities have been obtained even at the clinical level using $1-10 \times 10^6$ units daily with relatively crude preparations, less than 1% of which was human interferon. The purified, homogeneous human fibroblast interferon of the present invention can be utilized in the same manner as the previously employed crude preparations with adjustments in the dosage to provide the equivalent desired level of interferon units. While the compositions and processes of the present invention have been illustrated with starting materials derived from induced cell cultures of human fibroblastoid cells it is within the skill of the art to utilize crude interferon obtained by expression of recombinant microorganisms transformed with plasmids containing DNA coding for human fibroblast interferon as starting material.

The process and product aspects of this invention are further illustrated by reference to the following Examples. All interferon titers are expressed in terms of reference units/ml or units/mg against a reference standard for human leucocyte interferon (GO23-901-527) provided by the National Institutes of Health as determined by the assay procedure described in U.S. Pat. No. 4,241,174 incorporating a two hour incubation of human Ag 1732 cells with fibroblast interferon prior to virus challenge.

EXAMPLE 1

1.5 liter of crude fibroblast interferon (20,000 units/ml; 1 mg protein/ml) were mixed with 0.27 volumes of saturated NaCl-solution ($\sim 6.3$M) by end over end rotation of the bottle. This solution was pumped through Blue Dextran Sepharose (35 ml) packed in a 50 ml polypropylene syringe equipped with a porous polyethylene disk at the bottom (100 ml/hr or 20 cm/hr linear flow rate). The charged resin was washed in sequence with 200 ml of 1M NaCl containing 0.05M sodium phosphate buffer (pH 7.2); 500 ml of 1M NaCl containing 0.05M sodium phosphate (pH 7.2) and 75 ml of ethylene glycol and finally eluted with 500 ml of 4M NaCl containing 0.05M sodium phosphate (pH 7.2) and 250 ml ethylene glycol. About 90% of the interferon came down in a peak with the front of the 50% ethylene glycol. The specific activity in the peak maximum, where more than 50% of the total interferon eluted, was $1 \times 10^7$ units/mg.

PREPARATION OF THE BLUE DEXTRAN RESIN

Fifty grams of packed Sepharose 4B were washed with 1 liter of water and resuspended in 50 ml of distilled water. Fifteen grams of finely divided cyanogen bromide were added to the slowly stirred solution and the pH was immediately adjusted to and maintained at $11 \pm 0.2$ by dropwise addition of 10N NaOH. Temperature was maintained at $20 \pm 5°$ C. by small additions of crushed ice. When the reaction had subsided (15-20 min) about 1 vol. of ice-water was added, the suspension transferred into a Buchner funnel and further washed with 5 volumes of 0.01N HCl.

The activated resin was immediately suspended in 50 ml of 0.4M sodium carbonate buffer (pH 9.5) containing 1.00 g of dissolved Blue Dextan and rotated overnight at 4° C. in a round bottom flask. The resin was then washed with 10 volumes of 1M NaCl, 2 vol. of 50% ethylene glycol containing 1M NaCl and 0.05M sodium phosphate (pH 7.2), left overnight in the 50% ethylene glycol, washed with 1 vol. 80% ethylene glycol and 5 vol. Gibco #11 MEM culture medium containing 5% fetal calf serum and left in this medium overnight at 50° C. After further washings with 80% ethylene glycol containing 1M NaCl (3 volumes) and then with culture medium containing 5% fetal calf serum (2 volumes) the resin is then slurried in culture medium (MEM) containing 5% fetal calf serum and packed in a column for use.

By measurement of the absorption at 280 nm of the first wash it was estimated that 0.7–0.8 g Blue Dextran/50 ml resin had been coupled.

EXAMPLE 2

Concanavalin A Affinity Chromatography 50 ml of Concanavalin A-Sepharose which is equilibrated with PBS buffer containing 0.1M alpha-methylmannoside was packed in a 50 ml polypropylene syringe equipped with a polyethylene disk frit. It was loaded at 180 ml/hr or 35.5 cm/hr linear flow rate with 1.25 liters of crude interferon (20,000,000 units) having a specific activity of $2 \times 10^4$ units/mg. The charged column was washed with 150 ml of PBS buffer and 600 ml of PBS buffer containing 0.1M of alpha-methylmannoside. Interferon was finally eluted with the above buffer containing 50% ethylene glycol. Yield of procedure 9% (1.8 million units) with a specific activity of about $1 \times 10^7$ units/mg. A broader cut including additional fractions yielded 15% (3 million units) with a specific activity of $2-4 \times 10^6$.

EXAMPLE 3

HPLC with Con A Eluent

A total of 120 ml of eluent from the Con A column (2,500,000 units; approx. $2-4 \times 10^6$ units/mg) was applied directly to a Chromegabond 10μ (E. S. Industries) cyclohexyl-column (4.6×300 mm) which had been equilibrated with pyridine formic acid (8%/8%; v/v) containing 20% isopropanol (Buffer A) at flow rates in the range 0.4–0.8 ml/min keeping the maximal backpressure below 4500 psi. The system used for the high performance liquid chromatography procedures was essentially that described by Bohlen et al., supra.

A 4 hour gradient from equilibrating buffer A to final buffer B (pyridine 8%-formic acid 8% containing 25% isopropranol+20% n-butanol) was run at 0.4 ml/min (0–25% B, 32 min; 25–60% B, 225 min; 60–100% B, 63 min). Fractions of 2.0 ml were collected. A pool comprising fractions 26–29 (2,000,000 units) in the center of the activity peak was taken and diluted with pyridine-formic acid (8 ml+4 ml pyridine-formic acid). This solution was applied through the pump to a Chromegabond 10μ octyl column (4.6×300 mm). The elution conditions were the same as for the cyclohexyl column above. The specific activity in the center of the activity peak was approximately $4 \times 10^8$ units/mg with a total yield of purified human fibroblast interferon of 1,000,000 units.

It should be noted that the elution position of the interferon on both the cyclohexyl and octyl columns is very close to the main central peak when interferon purified on a Con A is subject to HPLC on either column. If the first HPLC step is carried out on an octyl column the interferon elutes right before the main central peak, while it elutes immediately after that peak under the same chromatography conditions on the cyclohexyl column.

EXAMPLE 4

HPLC With Blue Dextran Sepharose Eluent (A) A total of 125 ml of pooled interferon eluted from the Blue Dextran Sepharose column (30,000,000 units; $1 \times 10^7$ units/mg) were pumped on a 4.6×300 mm. Chromegabond 10μ octyl column which had been pre-equilibrated with 1M NaC containing 50% ethylene glycol. Immediately after sample application A-buffer (pyridine-formic acid, 8%/8%, plus 20% isopropanol and 3.3% n-butanol, v/v) was pumped on the column. A gradient to B-buffer (pyridine-formic acid 8%/8% plus 25% isopropanol and 20% n-butanol) with the following program was run at a flow rate of 0.45 ml/min.: 0–25% B-30 min.; 25–55% B, 190 min; 55–100% B, 20 min, then 100% B was run for another 60 min. Interferon activity was found to coincide essentially with a single protein peak found in tubes 18–23 (each tube contained 1.5 ml of eluent.)

(B) When approximately one-fourth the load in run (A) above was applied to the same column and the elution conditions used for the cyclohexyl column in Example 3 were employed interferon activity was found to coincide with a protein peak found in tubes 24–26.

(C) Using the same loading, gradient program and linear flow rate as in (A) and the A and B buffers used in (B) with a 9.6×500 mm Chromegabond octyl column which thus provided about 1/9th the loading per column volume, and resulted in a better separation quality.

(D) The material exhibiting the highest specific activity ($4 \times 10^8$ units/mg) from run (A) above was rechromatographed on a MN cyanopropyl column using 8% pyridine/8% formic acid 0–40% n-propanol (v/v) with a 1 hour gradient at 0.3 ml/minute to provide a symmetrical main peak.

EXAMPLE 5

NaDodSO$_4$ Polyacrylamide Gel Electrophoresis of Purified Human Fibroblast Interferon Samples of purified human fibroblast interferon obtained from Example 3 were run on 12.5 or 15% (NaDodSO$_4$)polyacrylamide gels in Tris/glycine buffer with 1 μg of protein for the run. After electrophoresis, a single band was obtained upon staining with Coomassie blue. The same sample material was run in a parallel gel and the gel sliced for antiviral assay. The maximum of the antiviral activity coincided with the center of the stained band. A molecular weight of about 20,500 was determined using bovine serum albumin (BSA), chymotrypsin, cytochrome C and ribonuclease as standards. The relative mobility of the human fibroblast band was the same whether mercaptoethanol was in the sample or not.

Samples from procedures (A), (B) and (C) of Example 4 showed as major band the 20,500 MW band, which when gels were sliced and assayed coincided with the center of the activity peak. The second strongest band (10,500 MW/20–50% of total material as estimated from the staining intensity) varied from sample to sample and had no antiviral activity. If samples were not treated with mercaptoethanol, a 40,000 MW band could be observed, which had borderline activity. Amino acid analysis of the 20,000 and 40,000 bands were indistinguishable while the analysis of the 10,000 band was very significantly different.

Electrophoresis of a sample from procedure (D) of Example 4 provided a single band which had a molecular weight of about 20,500 and a specific activity of $4 \times 10^8$ units/mg. An amino acid analysis of this homogeneous peptide carried out on a 24 hour hydrolysate in 6N HCl gave the following values relative to leucine taken arbitrarily as 25.0.

| | |
|---|---|
| Asx | 15.4 ± 0.2 |
| Thr* | 7.8 ± 0.3 |
| Ser* | 7.7 ± 0.2 |
| Glx | 24.1 ± 0.4 |
| Pro | 2.8 ± 0.4 |
| Gly | 4.9 ± 0.3 |
| Ala | 11.8 ± 0.4 |
| Cys | n.d. |
| Val | 6.9 ± 0.1 |
| Met | 2.8 ± 0.4 |
| Ile | 8.7 ± 0.1 |
| Leu | 25.0** |
| Tyr | 9.6 ± 0.2 |
| Phe | 7.3 ± 0.1 |
| His | 4.5 ± 0.1 |
| Lys | 11.6 ± 0.4 |
| Arg | 8.8 ± 0.4 |
| Trp | n.d. |

*These values are uncorrected for losses during hydrolysis.
**Arbitrary value
n.d. = not determined

EXAMPLE 6

Parenteral Dosage Form with Homogeneous Human Fibroblast Interferon

A total of 1.5 mg of homogeneous human fibroblast interferon having a specific activity of $4 \times 10^8$ units/mg is dissolved in 25 ml of 5% normal serum albumin (human) USP, the solution passed through a bacteriological filter and the filtered solution aseptically subdivided into 100 vials. Each vial contains $6 \times 10^6$ units of the pure interferon suitable for parenteral administration. The vials are preferably stored in the cold ($-20°$ C.) prior to use.

EXAMPLE 7

Blue Dextran Sepharose (a) Five liters of culture supernatant containing 19,400 units/ml of fibroblast interferon were filtered through a 0.3μ Pall Ultipor filter (No. DFA 3001BPP) and then applied to a column containing a bed volume of 275 ml of Blue Dextran-Sepharose. The supernatant was adjusted to 1.25M NaCl by the addition of 1,350 ml of a saturated solution of NaCl (6.3M) and pumped onto the column at a flow rate of 360 ml/hr. About 4-6% of the interferon passed through the column in the flow-through fraction that was not retained by the column.

(b) The column was then washed with 1,300 ml of a solution containing 15% ethylene glycol, 1M NaCl, and 0.02M sodium phosphate (pH 7.2) at a flow rate of 420 ml/hr. About 1% of the interferon applied to the column was found in this fraction.

(c) Interferon is eluted with a solution containing 50% ethylene glycol, 1M NaCl, and 0.02M sodium phosphate (pH 7.2) at a flow rate of 420 ml/hr. Little interferon was eluted in the first 200 ml after beginning elution with 50% ethylene glycol. Most of the interferon applied to the column was eluted in the next 300 ml eluted. Relatively little interferon was found in the next 350 ml eluted. The protein and interferon in the fractions was as follows:

| Fraction Number | Fraction | Protein | Interferon Titer (units/ml) | Specific Activity (units/mg) |
|---|---|---|---|---|
| 0 | 0-200 ml | Not Done | 122 | — |
| 1 | 200-250 | 43 μg/ml | 380,000 | $9.02 \times 10^6$ |
| 2 | 250-300 | 82 μg/ml | $1.164 \times 10^6$ | $1.42 \times 10^7$ |
| 3 | 300-350 | 63 μg/ml | 772,000 | $1.23 \times 10^7$ |
| 4 | 350-400 | 62 μg/ml | 194,000 | $3.13 \times 10^6$ |
| 5 | 400-450 | 49 μg/ml | 97,000 | $1.97 \times 10^6$ |
| 6 | 450-500 | 41 μg/ml | 36,400 | $8.87 \times 10^5$ |

The interferon from the 50% ethylene glycol elution was recovered in greater than 90% yield. The actual yield recovered was calculated as 114%; the greater than 100% is ascribed to assay variability. The total interferon recovered in the last elution between 200-450 ml ($133 \times 10^6$ units) was used for high performance liquid chromatography on Lichrosorb RP-8.

HPLC PURIFICATION INCLUDING DIPHENYL COLUMN

Fractions 1-5 from the Blue Dextran Sepharose affinity column (250 ml; $130 \times 10^6$ Units; specific activity $0.8 \times 10^7$ units/mg) were pumped on a $9.5 \times 500$ mm RP-8 column (ES Industries, Marlton, N.J.) at a flow rate of 4 ml/min. Buffer A (pyridine/formic acid/2-propanol/n-butanol 8%/8%/20%/2.5%) (v/v) was pumped through the column then at a flow rate of 2 ml/min for 12 min. Subsequently the following gradient was run to B buffer (pyridine/formic acid/2-propanol/n-butanol, 8%/8%/25%/25%) (v/v) at a flow rate of 1.25 ml/min: 10-20% B in 18 minutes; 20-29% B in 57 minutes; 29% B isocratic for 27 minutes; 29-30% B for 3 minutes; 30-100% B for 36 minutes followed by a 54 minute wash at 100% B.

The interferon activity emerged in the isocratic region of the gradient and coeluted with a peak detected with the Fluram (fluorescamine-Hoffman-La Roche Inc., Nutley, N.J.) monitoring system. $45 \times 10^6$ units of interferon were recovered (=35% yield) and a specific activity of $2 \times 10^8$ units/mg was obtained for the pool (50 ml). After 2 months of storage in stoppered polypropylene vials at $-20°$ C. the activity had dropped to 10% of the value after the RP-8 step. No protein was lost.

The 50 ml pool from the previous RP-8 column (specific activity $\sim 0.2 \times 10^8$ units/mg) was mixed with 1 ml thiodiglycol and 20 ml n-propanol. A total of $4.26 \times 10^6$ units was found in the assay for this mix. To this were added 100 ml of 0.1% Triton X-100/0.3% thiodiglycol. This mix assayed to $5.1 \times 10^6$ units total and was pumped on a 5 μ/80 Å 4.6×250 mm Spherisorb CN column (Laboratory Data Control, Riviera Beach, Fla.), which had previously been equilibrated with a 8% pyridine/8% formic acid mix, at a flow rate of 1.5 ml/hr. The following gradient was run to B-buffer (=equilibrating buffer containing 50% n-propanol) at a flow rate of 0.5 ml/min: 0–25% B in 30 min; 25–50% B in 210 min; equilibration with starting buffer for 30 min. The interferon activity emerged together with the only peak observed. $4.2 \times 10^6$ units were recovered (82%) in 3 fractions (1 ml ea.).

The above pool representing 69% of the total protein applied onto the first cyano column was mixed with 2 ml of 0.1% Triton X-100 and pumped onto the same cyano column used above. The same gradient as above with half the total gradient time was run.

All activity ($11.75 \times 10^6$ units-280% recovery) eluted together with the only peak.

The interferon activity pool from the second cyano column (4 ml) was pumped onto a 4.6×250 mm diphenyl column at a rate of 1.5 ml/min. The column had previously been precycled with a linear 2 hr gradient from buffer A to B (same buffer as for the cyano column) and equilibrated with A buffer.

The following gradient was run at 0.5 ml/min: 0–25% B in 22 min; 25–50% in 98 min. The second peak, which eluted while the gradient instrument indicated 33% B buffer, coincided with the interferon activity plot. A total of $2.6 \times 10^6$ units (22%) and 40 μg of protein eluted with this peak.

A sample of the center fraction of the resulting interferon peak was analyzed for amino acid composition under varying hydrolysis conditions. The results are summarized below:

| All hydrolyses in 5.7N HCl in acid washed evacuated glass tubes. Sample buffer and HCl blanks are substituted | | | |
|---|---|---|---|
| Asx | 15.4 | 17.6 | 17.95 | 15.2 |
| Thr | 7.8 | 8.6 | 8.4 | 7.3 |
| Ser | 7.7 | 8.3 | 9.1 | 9.9 |
| Glx | 24.1 | 21.1 | 21.4 | n.d. |
| Pro | 2.8 | n.d. | n.d. | 3.36 |
| Gly | 4.9 | 6.9 | 6.6 | 7.4 |
| Ala | 11.8 | 10.7 | 10.7 | 9.9 |
| Cys | n.d. | 3.96 | 3.4 | n.d. |
| Val | 6.9 | 7.84 | 8.2 | 6.9 |
| Met | 2.8 | 4.5 | 4.5 | 3.7 |
| Ile | 8.7 | 8.6 | 8.9 | 7.8 |
| Leu | 25.0** | 25** | 25** | 25** |
| Tyr | 9.6 | 10.3 | 9.0 | 8.1 |
| Phe | 7.3 | 9.5 | 9.8 | 9.0 |
| His | 4.5 | 7.5 | 6.9 | 6.1 |
| Lys | 11.6 | 12.3 | 11.8 | 11.25 |
| Arg | 8.8 | 11.25 | 10.6 | 8.8 |
| Trp | n.d. | n.d. | n.d. | 2.93 |
| | | 24 hrs. 0.2% | 48 hrs. 0.2% | 24 hrs. 2% |
| Conditions | | TGA | TGA | TGA |

*These values are uncorrected for losses during hydrolysis.
**Arbitrary value

HEXOSAMINE ANALYSIS

I. Standardization

Standard solutions of glucosamine (GlcN), galactosamine (GalN), amino acids and mixtures of these were prepared and analyzed in order to determine the retention times of the components and to determine the relationship between peak height and amount of component present. A linear relationship was demonstrated for the standards tested over the range 0–20 nmole for hexosamine and 0–500 pmoles for amino acids. The retention times for the hexosamines and amino acids were fairly reproducible ($\pm \frac{1}{2}$ min) and identification of the components could easily be made.

| Retention Times | |
|---|---|
| Tyrosine (TYR) | 8 min |
| Phenylalamine (PHE) | 9.5 min |
| Glucosamine (GlcN) | 17 min |
| Galactosamine (GalN) | 19.5 min |
| Lysine (LYS) | 27 min |
| Histidine (HIS) | 31 min |

II. Sample Preparation

The interferon to be assayed, utilizing the eluent from the center peak fraction of the diphenyl column of Example 7, was transferred to a glass hydolysis tube as folows: Fifty (50) microliters of the interferon solution in its elution buffer was transferred to the glass hydrolysis tube with a plastic tipped pipet. The buffer was removed by evaporation in a vacuum desiccator and then 200 microliters of 5.7N hydrochloric acid containing 0.2% thioglycolic acid was added and the tube sealed under vacuum. Hydrolysis was carried out at 110° C. for 6, 14 and 24 hrs after which the tube was opened and the acid removed via vacuum desiccator (3 hrs). To the tube was added 300 microliters of sample buffer (pH 2.2 sodium citrate buffer, 0.2M in sodium ion). The solution, after vigorous stirring on a Vortex mixer was removed and stored in plastic sample vials for analysis.

III. Analysis

The conditions for analysis which are outlined are a modification of generally accepted methodology. The modification is the use of microbore column of high efficiency resin with Fluram detection. The basic technique is to apply the sample hydrolysate to the resin and elute the column so as to resolve the hexosamines and several amino acids. These are reacted with Fluram as they emerge from the column and resulting fluorophores measured with a flow cell fluorometer. The series of analyses run for each sample were the sample hydrolysate, a standard mixture of hexosamine and amino acids (150 pmoles hexosamines and 50 pmoles of amino acids) and a buffer blank hydrolysate.

IV. Calculations

The calculation of hexosamine content and amino acid content were made by generally accepted methods.

Hexosamine: The peak height of the standard glucosamine (150 pmoles) was measured. The peak height of the sample hexosamine was then compared to that of the standard to give the amount of hexosamine in the sample:

$$\frac{\text{height of sample hexosamine}}{\text{height of standard hexosamine}} \times 150 \, p\text{mole} = p\text{moles hexosamine in sample}$$

The value represents the hexosamine content in portion of the hydrolysate used for the assay. This was usually 100 microliters out of a total of 300 microliters of hydrolysate.

Thus, the total hexosamine in the sample hydrolyzed was obtained by multiplication by a factor of 3.

Amino Acids: For the amino acids a slightly different procedure was used. Standard curves for each amino acid were determined by plotting peak heights against pmoles of amino acid. The peak heights of the amino acids in the sample hydrolysate are plotted on their respective curves and the pmoles determined from the curves.

Residue Calculation: From the amino acid content of fibroblast interferon, it was known that 9 residues of tyrosine are present. This was used to calculate the residues of glucosamine.

$$\frac{9}{(pmoles\ tyrosine)\ (hydrolysate)} \times (pmoles\ GlcN)\ (hydrolysate) = residues\ GlcN$$

RESULTS

A. The interferon sample was hydrolyzed 24 hrs at 110°. As indicated by amino acid analysis, the sample was approximately 90 pmoles of interferon.

For assay the hydrolysate was dissolved in 300 microliters of buffer and 100 microliters put on the column. The results indicated the following:

|  | pmoles (100 microliters) | pmoles (total in sample) | Residues |
| --- | --- | --- | --- |
| Tyr | 158 | 474 | 9.06 |
| Phe | 172 | 516 | 9.87 |
| GlcN | 33 | 99 | 1.89 |
| GalN | 0 | 0 | 0 |
| Lys | 215 | 645 | 12.3 |
| His | 112 | 336 | 6.4 |

The 24 hr sample indicated that interferon contains 1.89 residue of glucosamine. There was no galactosamine or mannosamine which coelute at the same point.

B. To test time effect on release of glucosamine, two more hydrolysis were carried out at different time durations, 6 hr hydrolysis and 14 hrs.

The reason is that acid destroys some of the hexosamine in hydrolysis and this amount must be accounted for.

Thus, if we run several times of hydrolysis and plot hexosamine vs. time of hydrolysis we should get a straight line which, when plotted back to zero, gives us the true hexosamine value.

The 14 hr and 24 hr results were plotted and used to extropolate to time zero thereby providing an approximate value of about 3 residues of galactosamine.

| not used → | 6 hr hydrolysis | glucosamine | 0.7 residues |
| --- | --- | --- | --- |
|  | 14 hr hydrolysis | glucosamine | 2.4 |
|  | 24 hr hydrolysis | glucosamine | 1.89 |
| intercept = | ≈ 3.1 residues |  |  |

POSSIBLE ERROR IN RESULT

Tryptophan was found to coelute with glucosamine in the conditions used. Its fluorescence yield is only about 1/10 that of glucosamine so the error is small.

Fibroblast interferon contains 3 residues of tryptophan
  Found glucosamine = 3 residues
Since fluorescence is 1/10 of glucosamine-correction factor = 3 × 1/10 = 0.3
Thus, approximate glucosamine in fibroblast interferon = 2.7 residues.

ENDGROUP DETERMINATION

A sample (90 pmol) of the center fraction of the diphenyl column interferon peak was dansylated according to Hartley, Biochem. J. 119, 805 (1970), hydrolyzed for 18 hours with 5.7N HCl and analyzed using the HPLC conditions reported by Wilkinson, J. Chromat. Sci. 16, 547 (1978) with a Schoeffel Fluorometer for detection. The expected number of $\epsilon$-DNS-Lys ($\sim$11) was found and 70-80% of the amount of Met as N-terminus (amount expected from the protein determination by amino acid analysis). Further observed peaks were either also found in the buffer control or did not correspond to elution positions of known common amino acids.

TRYPTIC MAPS OF HUMAN LEUKOCYTE AND FIBROBLAST INTERFERON

In order to be able to compare tryptic maps of leukocyte and fibroblast interferon, digestions of one of the leukocyte interferon species ($\gamma_1$) and a sample of fibroblast interferon (center fraction of the diphenyl column fibroblast interferon peak) were done side by side under identical conditions. A LiOH/Bicine buffer rather than a carbonate-based buffer was used for solubility reasons with the fibroblast material and to be able to include $CaCl_2$ in the buffer. The $CaCl_2$ is important to limit autolysis of the trypsin and thus limit the relative contribution of the never completely suppressible chymotryptic activity in trypsin preparations.

The following protocol was used:
1. Digestion:

Material (150 pmol fibroblast interferon and 160 pmol leukocyte interferon) was freeze-dried in 1.5 ml conical polypropylene centrifuge tubes and redissolved in 20 μl each of 0.1M Bicine/LiOH/10 mM $CaCl_2$ (pH 8.0). TPCK trypsin purchased from Worthington (2 μl of the following solution: 0.1% trypsin in 1 mM HCl was diluted 1/25 with the above Bicine/LiOH buffer) was added to the protein solutions. After 3 hrs incubation at 37° C., another 2 μl of the enzyme solution was added and incubation at 37° C. continued overnight. After a total incubation time of 18 hrs, 2-mercaptoethanol was added up to a concentration of 5% and the digest kept for another hour at 37° C.

Pyridine-formate buffer (420 μl 0.14M pyridine/0.5M formic acid; pH 3) was added and an aliquot (300 μl) taken for chromatography. The remaining solution and the second sample were flushed with argon and kept at −20° C. A blank sample was obtained by running the digestion with no protein other than trypsin.

Chromatography:

Sample solution (300 μl) was injected onto the column (Altex Ultrasphere Octyl, 4.6×25 cm) with a loop injector (Rheodyne). After 10 min, a linear 3 hr gradient from 0.1M formic acid/0.03M pyridine (buffer A) to buffer A containing 40% n-propanol was run. The column flow rate was 0.5 ml/min and the effluent was monitored with Fluram.

Four different samples were run under identical conditions:
1. leukocyte interferon digest
2. fibroblast interferon digest
3. a mix of Item 1 and 2 (50/50)
4. a blank digest containing no protein except trypsin The Maps:

No peptide common to both interferons was found. After overnight standing at pH 3/−20° C., some earlier eluting peaks ceased and later eluting peaks appeared. This is due to oxidation of Cys peptides, which proceeds even at the low pH.

Sequencing

An amount of 1.25 nmol was sequenced in a Beckman spinning cup sequencer modified according to Wittmann-Liebold, Z. Physiol. Chem. 354, 1415 (1973), and the 12th Miles Inter. Symposium (in press) using Polybrene as carrier and a Quadrol buffer system according to Hunkapillar and Hood, Biochemisty 17, 2124 (1978) with a double cleavage/double coupling program. The N-terminus (Met) was confirmed. Residue #2 (Ser) according to Hunkapillar could not be identified. The sequence 3–10 reported by Hunkapillar could be confirmed ($Tyr^3$-$Asn^4$-$Leu^5$-$Leu^6$-$Gly^7$-$Phe^8$-$Leu^9$-$Gln^{10}$).

The diphenyl column used in this example may be prepared as follows:

EM Lichrosphere Si-100 (10 μm, 10 nm pore size; Ace Scientific, Linden, N.J. silica support was soaked in 6N HCl (10:1 v/w) for 24 hr with occasional shaking. The support was washed on a sintered glass filter with water until the wash was neutral and then washed with acetone and methanol to remove the water. After drying in vacuum overnight, the support (10 g) was refluxed in dry toluene (100 ml) containing 10 ml of dichlorodiphenylsilane (dipheny) (Silar Lab., Scotia, N.Y.) for 6 hr. The bonded support was removed from the toluene solution with a sintered glass filter and washed with 200 ml of toluene. Following this, the bonded support was treated in a Soxhlet extractor sequentially with 250 ml of toluene, acetone and methanol (all solvents from Burdick and Jackson, Muskegon, MI) for 8 hr each. The support was then capped with trimethylchlorosilane by the same procedures as above.

The bonded support was packed in 4.6×250 mm stainless steel columns (Rainin Instruments, Ridgefield, N.J. Packing was carried out at 5,000 psi with a Haskell air-driven pump (Burbank, Ca.) using a mixture of chloroform (10.7 ml) and n-butanol (2.3 ml) to suspend 3 g of support. The columns were then washed with ethanol (75 ml).

EXAMPLE 8

Production of Fibroblast Interferon

Crude fibroblast interferon was produced from human fibroblasts (cell line GM 2504A) grown in 850 $cm^2$ roller bottles. Confluent monolayers were induced with 25 mls of the following media per bottle:
5% heat inactivated fetal calf serum
5% μg/ml gentamicin
25 μg/ml Poly I. Poly C
10 μg/ml Cyclohexinide
in F 11 tissue culture medium (Gibco).

After 4 hours, Actinomycin D was added to a final concentration of 1 μg/ml.

After 2 additional hours, the media was poured off and the roller bottle rinsed with phosphate buffered saline. 50 mls of the following serum free media was added to each bottle: 50 μg/ml gentamicin in F 11 and the cells were incubated overnight at 37° C.

The next morning the medium was poured into a polypropylene container to provide crude fibroblast interferon.

Purification of Crude Fibroblast Interferon

Step 1

5L. Crude fibroblast interferon was made 1M in sodium chloride by the addition of saturated sodium chloride (ca. 6.1M at room temperature). This material was passed through a column of Blue Sepharose-4B (bed volume=20-25 ml, diameter 2.5 cm, 2.5 mls/min. - Pharmacia Fine Chemicals, New Jersey). The crude material was kept on ice while loading.

After loading, the column was washed 2.5 ml/min with 250 mls of the following solution:
30% ethylene glycol
1M sodium chloride
50 mM $Na_2H$ $PO_4$, pH 7.2;

Finally, the interferon was eluted at 2.5 ml/min. with 250 ml of the following solution:
50% ethylene glycol
1M sodium chloride
50 mM $Na_2H$ $PO_4$, pH 7.2;
Typical assay results:
5% activity in flow thru
10% activity in 30% wash
85% activity in 50% wash.

Purification of Crude Fibroblast Interferon

Step 2

Peak fractions from the first Blue Sepharose column were pooled and diluted to 10% ethylene glycol with the following solution:
2M sodium chloride
50 mM $Na_2H$ $PO_4$, pH 7.2.

This material was loaded on a Blue Sepharose column (20-25 ml bed volume, 2.5 cm diameter, 2.5 ml/min). It was washed with 250 ml of:
2M sodium chloride
50 mM $Na_2H$ $PO_4$, pH 7.2
30% ethylene glycol.
It was eluted with:
50% ethylene glycol
2M sodium chloride
50 mM $Na_2H$ $PO_4$, pH 7.2.
Typical assay results:
10% activity in flow thru
30% activity in 30%
60% activity in 50%.

PURIFICATION OF FIBROBLAST INTERFERON BY HPLC

Sample: The first sample used was the 50% ethylene glycol cut from Blue-Sepharose. Later samples were ones that had been run through Blue-Sepharose twice, in which case interferon in either the 30% or 50% ethylene glycol cut could be used.

HPLC

A 25×0.46 cm RP-8 (Lichrosorb, EM) was used. The column was first washed with water and then the Blue-Sepharose eluate was pumped on. The HPLC column was run at 22 ml/hr with a step-wise gradient of n-propanol, at a constant pH of 4.2 maintained with 1M formic acid - 0.8M pyridine. A 5 ml mixing chamber was used before the pump and thereby smoothed out the buffer steps.

| % n-Propanol | Time (min) |
|---|---|
| 1. 0 | 10 |
| 2. 30% | 40 |
| 3. 32% | 40 |

Then washed with 60% n-propanol and re-equilibrated with 0% for next run.

Interferon eluted at the end of the 32% step (between 80 and 90 min). This material was homogeneous as determined by SDS gel electrophoresis staining with Coomassie Blue or prelabeling the sample with Fluram.

Amino acid analyses (24 hour hydrolysis —0.2% TGA - 5.7 NHCl) were carried out on nine separate samples comprising four separate preparations. The average amino acid composition is set forth below with values relative to leucine taken arbitrarily as 22.0. The results were as follows:

|  | Residues | Average Deviation (n = 9) |
| --- | --- | --- |
| Aspartic Acid | 15.1 | ±0.7 |
| Threonine* | 7.0 | ±0.5 |
| Serine* | 7.5 | ±0.5 |
| Glutamic Acid | 22.2 | ±0.5 |
| Proline |  | Not determined |
| Cysteine | 3.0 | ±0.3 |
| Glycine | 6.9 | ±0.7 |
| Alanine | 7.4 | ±1.0 |
| Valine | 5.7 | ±0.5 |
| Methionine | 4.5 | ±0.7 |
| Isoleucine | 9.4 | ±0.1 |
| Leucine | 22 | (normalized) |
| Tyrosine | 8.8 | ±0.2 |
| Phenylalanine | 8.0 | ±0.3 |
| Histidine | 4.5 | ±0.1 |
| Lysine | 11.0 | ±0.6 |
| Arginine | 11.9 | ±0.7 |
| Tryptophan |  | Not determined |

*Not corrected for loss during hydrolysis.

Based on the several samples prepared by different procedures and analyzed at different times as set forth above in this and prior Examples, a representative amino acid analysis (±15%) for homogeneous fibroblast interferon utilizing a 24 hour hydrolysate in 6N HCl with 0.2% thioglycollic acid is as follows:

| Aspartic acid | 15.1 |
| --- | --- |
| Threonine* | 7.0 |
| Serine* | 7.5 |
| Glutamic acid | 22.2 |
| Proline | 3.0 |
| Cysteine | 3.0 |
| Glycine | 6.9 |
| Alanine | 7.4 |
| Valine | 5.7 |
| Methionine | 4.5 |
| Isoleucine | 9.4 |
| Leucine** | 22 |
| Tyrosine | 8.8 |
| Phenylalanine | 8.0 |
| Histidine | 4.5 |
| Lysine | 11.0 |
| Arginine | 11.9 |
| Tryptophan | 3.0 |

*Not corrected for loss during hydrolysis.
**Arbitrary value

EXAMPLE 9

Interferon Production

Crude fibroblast interferon was produced as described by Havell and Vilcek, Antimicrob. Agents Chemother. 2, 476 (1972) except that serum was omitted from the overnight induction medium.

Slab Gel Polyacrylamide Electrophoresis

Slab gel polyacrylamide electrophoresis was performed on a 5–15% polyacrylamide gradient or a 15% polyacrylamide gel in a Tris.glycine (pH 8.3) buffer in the presence of 0.1% sodium dodecyl sulfate (NaDodSO₄). Protein standards as well as interferon were incubated in 2% (w/v) NaDodSO₄ and 5% (v/v) 2-mercaptoethanol for 30 min at room temperature prior to electrophoresis. Gels were stained with Coomassie blue. Alternatively, proteins were labeled with fluorescamine. To samples dissolved in 20 µl of 50 mM lithium borate buffer, pH 9.3, containing 3% (w/v) NaDodSO₄, were added 10 µl of fluorescamine in acetone (1 mg/ml).

Detection of Amino Acids and Proteins by Fluorescence

Amino acid analyses were performed on a fluorescamine analyzer as described by Stein et al., Arch. Biochem. Biophys. 155, 203 (1973). Samples (0.5 µg) were hydrolyzed in 200 µl of constant boiling hydrochloric acid containing 0.1% thioglycolic acid for 24 h at 110° C. An automated fluorescence detection system of Bohlen, supra was used for monitoring peptides in column effluents. High performance liquid chromatography columns were obtained from EM Laboratories (Elmsford, N.Y.). Pyridine, acetic acid, and formic acid were distilled over ninhydrin, and water was purified by passage through activated charcoal and mixed-bed deionizer cartridges (Hydro Service and Supplies, Durham, N.C.). Column eluents were degassed in vacuo and stored under argon. Polypropylene tubes and laboratory ware were used for fractions containing interferon. Proteins were assayed by injection of samples into the fluorescamine peptide/protein monitoring system with bovine serum albumin as a standard. This method gave excellent reproducibility and sensitivity with nanogram quantities and was in agreement with quantitation of the purified interferon by amino acid analysis.

Automated Sequencing of Interferon

Automated Edman degradations were performed on a modified Beckman 890C sequenator. The modifications similar to published systems include an improved vacuum system, improved reagent and solvent delivery system, extensive solvent and reagent purification, and a device which automatically converts anilinothiazolinone to phenylthiohydantoin (PTH) derivatives of amino acids. Proteins are retained in the spinning cup with 6 mg of polybrene which, together with 100 nmoles of glycylglycine, has been subjected to 7 precycles of Edman degradation. PTH amino acids were analyzed by high performance liquid chromatography on DuPont Zorbax ODS or CN columns using 254 nm and 313 nm detection on a Waters Associates chromatograph. Peaks were integrated and gradient elution was controlled by a Spectra Physics SP4000 integration system. All PTH derivatives were detected at 254 nm, except for those of serine and threonine which were detected at 313 nm.

Purification of Human Fibroblast Interferon on Blue-Sepharose

Sodium chloride was added to medium containing interferon to make a final concentration of 1M and the solution was then pumped onto a 25 ml Blue-Sepharose CL-68 (Pharmacia) column at room temperature at a rate of 2.5 ml per minute. The unfractionated interferon was held on ice while loading. The column was washed with 250 ml of sodium phosphate buffer (50 mM Na₂HPO₄, adjusted to pH 7.2 with HCl) containing 1M NaCl and 30% ethylene glycol. The interferon was eluted with the same solution containing 50% ethylene glycol. Peak fractions of activity were pooled and stored at 4°

C. until used. Activity appeared to be stable for at least three months at 4° C. or in liquid nitrogen.

In preparations having a low initial titer, it was found that a second passage through Blue-Sepharose was required. In these instances, when a total of 25 liters of crude interferon had been chromatographed, the peak fractions from five columns were pooled and adjusted to 10% ethylene glycol, 2M NaCl and 50 mM $Na_2HPO_4$, pH 7.2. This material was then applied to another Blue-Sepharose column. The column was then washed with 250 ml of a sodium phosphate buffer (50 mM $Na_2HPO_4$, adjusted to pH 7.2 with HCl) containing 2M NaCl and 30% ethylene glycol. Some interferon eluted at this step. The remaining interferon was eluted with the same solution containing 50% ethylene glycol. Interferon that eluted from the second Blue-Sepharose column with both 30% and 50% ethylene glycol was satisfactory for use in the next step of the purification. The specific activity of the interferon deemed satisfactory for the HPLC step ranged from $3 \times 10^7$ to $3 \times 10^8$ units/mg of protein. The Blue-Sepharose was discarded after each run.

High Performance Liquid Chromatography

The interferon from the affinity chromatography was pumped onto a $25 \times 0.46$ cm Lichrosorb RP-8 (10 μm) column at 22 ml/h or 132 cm/hr. The column was eluted at 22 ml/h or 132 cm/hr with 1M formic acid/0.8M pyridine (pH 4.2) for 10 min and then with increasing concentrations of n-propanol in the same buffer. The steps were 30% n-propanol for 40 min, 32% for 40 min, 34% for 20 min, 41% for 20 min and 60% for 40 min. Interferon activity eluted only during the 32% n-propanol step. In this particular chromatogram, the interferon had been passed through Blue-Sepharose twice and, therefore, represented the major component. The purification is summarized in Table 1. Homogeneous interferon purified in this manner has a specific activity of $3 \times 10^8$ units/mg of protein.

TABLE 1
PURIFICATION OF HUMAN FIBROBLAST INTERFERON

|  | Total Units | Total Protein | Overall Recovery (units) | Specific Activity (units/mg) |
|---|---|---|---|---|
| Crude interferon | $7.4 \times 10^7$ | N.D. | 100% | N.D. |
| 50% ethylene glycol | $3.7 \times 10^7$ | 1.08 mg | 43% | $3.4 \times 10^7$ |
| HPLC | $1.1 \times 10^7$ | 33.8 μg | 15% | $3.2 \times 10^8$ |

N.D. - not determined

Polyacrylamide Gel Electrophoresis

Homogeneity of the preparation was determined by polyacrylamide gel electrophoresis in sodium dodecyl sulfate. A single protein band was obtained when the gels were stained with Comassie blue. An unstained track of the same slab gel was cut into 1 mm slices, and each slice was homogenized in 0.1 ml of a solution of complete Eagle's minimal essential medium containing 10% fetal calf serum, 12.5 mM HEPES (N-2-hydroxyethylpiperazine-N'-2-ethane-sulfonic acid), and 50 ug/ml of Gentamicin. Each fraction was assayed for interferon activity. A single peak of activity coinciding with the protein band was obtained.

As further proof of homogeneity, the purified interferon was labeled with fluorescamine. Again, a single (fluorescent) protein band was obtained. This latter technique rules out the presence of peptide and protein contaminants which might be undetected by the Coomassie blue staining procedure, since the gels are photographed immediately after electrophoresis without any washing steps.

Amino Acid Analysis

Amino acid analysis of the homogeneous fibrobast interferon was performed with 0.5 μg samples of interferon. These analyses are summarized in Table 2. The analyses were essentially the same for samples from four different HPLC preparations as well as from individual fractions corresponding to the center and sides of an interferon peak.

Proline and tryptophan were not determined on these samples, which were used for the sequence analysis reported below. However, other samples of fibroblast interferon, which were prepared by induction in the presence of serum, were extensively analyzed. They were found to have essentially the same composition, and in addition 3 residues of proline, 3 residues of tryptophan, 3 residues of glucosamine, and no residues of galactosamine or mannosamine.

TABLE 2
AMINO ACID COMPOSITION OF HUMAN FIBROBLAST INTERFERON

| Amino Acid | Residues |
|---|---|
| Aspartic Acid (Asn + Asp) | 15.1 ± 0.7 |
| Threonine* | 7.0 ± 0.5 |
| Serine* | 7.5 ± 0.5 |
| Glutamic Acid (Gln + Glu) | 22.2 ± 0.5 |
| Proline | Not Determined |
| Cysteine | 3.0 ± 0.3 |
| Glycine | 6.9 ± 0.7 |
| Alanine | 7.4 ± 1.0 |
| Valine | 5.7 ± 0.5 |
| Methionine | 4.5 ± 0.7 |
| Isoleucine | 9.4 ± 0.1 |
| Leucine | 22 |
| Tyrosine | 8.8 ± 0.2 |
| Phenylalanine | 8.0 ± 0.3 |
| Histidine | 4.5 ± 0.1 |
| Lysine | 11.0 ± 0.6 |
| Arginine | 11.9 ± 0.7 |
| Tryptophan | Not Determined |

Samples (0.5 μg) were hydrolyzed in 200 μl of constant boiling hydrochloric acid containing 0.1% thioglycolic acid for 24 h at 110° C. Average deviations (n = 9) are given in parentheses. Values are normalized to leucine = 22.
*Not corrected for loss during hydrolysis.

Sequence Analysis

The $NH_2$-terminal sequence analysis of 5.9 nmoles of human fibroblast interferon was carried out. A maximum yield of 1.8 nmoles of methionine at cycle 1 and 1.5 nmoles of leucine at cycle 5 was obtained. Since the routine yield of PTH-methionine in this laboratory is about 80%, the overall yield of the $NH_2$-terminal amino acid is about 40%. This figure agrees well with the yields of PTH-leucine at cycles 5, 6, and 9 assuming a repetitive yield of 92%. The high yield of $NH_2$-terminal methionine and the finding of a single sequence through 19 cycles strongly suggests that this is a single pure protein. The assignments of serine at positions 2, 12, and 13 were based on the detection of the "dehydroserine" derivatives on a DuPont Zorbax CN column. Although there appears to be a tyrosine peak at position 17, a varying background peak is often seen in the PTH-tyrosine area of the chromatograms.

The excellent yields of PTH amino acids through position 10 were followed by a sudden drop at position 14. The drop in yields was apparently caused by the sequence Arg-Ser-Ser. A second more drastic drop in yields was encountered beyond position 19, perhaps due to a very hydrophobic stretch of amino acids.

The results indicate the following sequence for the NH$_2$-terminal sequence NH$_2$-Met-Ser-Tyr-Asn-Leu-Leu-Gly-Phe-Leu-Gln-Arg-Ser-Ser-Asn-Phe-Gln-... -Gln-Lys ...

We claim:

1. Human fibroblast interferon having:
   (a) a specific activity of about $4 \times 10^8$ units/mg as measured by a cytopathic effect inhibition assay;
   (b) an apparent molecular weight of about 20,500 by sodium dodecylsulfate polyacrylamide gel electrophoresis;
   (c) an amino acid composition ($\pm 15\%$) based on 24 hour hydrolysis in 6.0N HCl with 0.2% thioglycolic acid as follows:

|     |      |
| --- | ---- |
| Asx | 15.1 |
| Thr* | 7.0 |
| Ser* | 7.5 |
| Glx | 22.2 |
| Pro | 3.0 |
| Gly | 6.9 |
| Ala | 7.4 |
| Cys | 3.0 |
| Val | 5.7 |
| Met | 4.5 |
| Ile | 9.4 |
| Leu** | 22.0 |
| Tyr | 8.8 |
| Phe | 8.0 |
| His | 4.5 |
| Lys | 11.0 |
| Arg | 11.9 |
| Trp | 3.0; | wherein values indicated by* are uncorrected for losses during hydrolysis and the value is indicated by** is an arbitrary value;

(d) a partial amino acid sequence

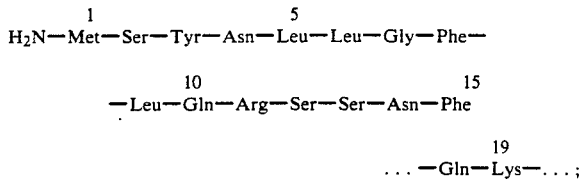

and (e) a maximum of 3 residues of glucosamine and no residues of galactosamine or mannosamine per molecule of human fibroblast interferon;

which interferon is free of sodium dodecyl sulfate and is homogeneous as determined by obtaining a single band in sodium dodecylsulfate polyacrylamide gel electrophoresis, a constant specific activity, a single peak in HPLC with activity and protein levels superimposable and a single amino-terminal amino acid sequence.

2. A pharmaceutical preparation suitable for parenteral administration for treatment of viral and neoplastic disease states which preparation comprises an effective amount of the human fibroblast interferon of claim 1 and a conventional pharmaceutical parenteral carrier material.

* * * * *